(12) United States Patent
King et al.

(10) Patent No.: US 9,782,207 B2
(45) Date of Patent: Oct. 10, 2017

(54) BONE ANCHOR LOCKING DEVICE

(71) Applicants: Challis Avery King, Florence, SC (US); Dale Whipple, Acworth, GA (US); William Carlton Tally, Athens, GA (US)

(72) Inventors: Challis Avery King, Florence, SC (US); Dale Whipple, Acworth, GA (US); William Carlton Tally, Athens, GA (US)

(73) Assignee: Amendia, Inc., Marietta, GA (US)

( * ) Notice: Subject to any disclaimer, the term of this patent is extended or adjusted under 35 U.S.C. 154(b) by 594 days.

(21) Appl. No.: 14/466,581

(22) Filed: Aug. 22, 2014

(65) Prior Publication Data
US 2016/0000485 A1 Jan. 7, 2016

Related U.S. Application Data

(60) Provisional application No. 62/020,863, filed on Jul. 3, 2014.

(51) Int. Cl.
| A61B 17/80 | (2006.01) |
| A61B 17/86 | (2006.01) |
| A61B 17/84 | (2006.01) |
| F16B 41/00 | (2006.01) |
| A61B 17/70 | (2006.01) |

(52) U.S. Cl.
CPC .......... *A61B 17/8047* (2013.01); *A61B 17/80* (2013.01); *A61B 17/8033* (2013.01); *A61B 17/8042* (2013.01); *A61B 17/8052* (2013.01); *A61B 17/8057* (2013.01); *A61B 17/84* (2013.01); *A61B 17/86* (2013.01); *A61B 17/8695* (2013.01); *F16B 41/002* (2013.01); *A61B 17/7059* (2013.01)

(58) Field of Classification Search
CPC . A61B 17/7059; A61B 17/80; A61B 17/8033; A61B 17/8042; A61B 17/8047; A61B 17/8052; A61B 17/8057; A61B 17/84; A61B 17/86; A61B 17/8695; F16B 41/002
See application file for complete search history.

(56) References Cited

U.S. PATENT DOCUMENTS

| 6,261,291 | B1 | 7/2001 | Talaber et al. | |
| 7,410,496 | B2 * | 8/2008 | Derouet | A61B 17/8047 606/290 |
| 7,524,325 | B2 | 4/2009 | Khalili | |
| 7,857,839 | B2 | 12/2010 | Duong et al. | |
| 8,075,602 | B2 | 12/2011 | Lombardo et al. | |
| 8,328,856 | B1 | 12/2012 | Donahoe et al. | |

(Continued)

*Primary Examiner* — Larry E Waggle, Jr.
(74) *Attorney, Agent, or Firm* — David L. King

(57) ABSTRACT

A bone anchor locking device for receiving a bone anchor having a shank and an enlarged head, the device has a bone anchor, a dome and a conical split washer. The receiving portion has a base extending radially outward and inwardly to a wall. The dome has a center aperture sized to pass a bone anchor. The split washer has an inner conical surface sloped to slide and expand against at least a portion of the base on insertion of a bone anchor to allow a maximum diameter of a head of a bone anchor to pass and thereafter the split washer retracts overlying the maximum diameter of the head to prevent a bone anchor from backing out.

19 Claims, 10 Drawing Sheets

(56) References Cited

U.S. PATENT DOCUMENTS

| | | |
|---|---|---|
| 8,343,194 B2 | 1/2013 | Aflatoon et al. |
| 8,419,797 B2 | 4/2013 | Biedermann et al. |
| 8,486,116 B2 * | 7/2013 | Heilman ............ A61B 17/8047 606/286 |
| 8,702,762 B2 | 4/2014 | Jacene et al. |
| 2004/0210223 A1 * | 10/2004 | Pisharodi ........... A61B 17/8047 606/71 |
| 2009/0222051 A1 | 9/2009 | Pengo |
| 2012/0179212 A1 | 7/2012 | Jackson et al. |

* cited by examiner

BONE ANCHOR LOCKING DEVICE

TECHNICAL FIELD

The present invention is related to a bone anchor locking device and implants such as cervical plates generally.

BACKGROUND OF THE INVENTION

The use of locking devices to prevent bone anchors from loosening is well known in the art. Such anti-loosening devices are used on a variety of implants and plate type devices. The present invention provides an improvement in such devices.

SUMMARY OF THE INVENTION

A bone anchor locking device for receiving a bone anchor having a shank and an enlarged head, the device has a bone anchor, a dome and a conical split washer. The bone anchor receiving portion has a through hole sized for receiving and allowing the shank pass and holding the head. The receiving portion has a base extending radially outward and inwardly to a wall. The dome has a center aperture sized to pass a bone anchor. The dome is fixed to the wall and spaced above the base to create a domed chamber. The conical split washer is positioned in the domed chamber. The washer has an inner relaxed inner diameter smaller than the head of a bone anchor and an outer diameter larger than the center aperture of the dome and part of the base. The split washer has an inner conical surface sloped to slide and expand against at least a portion of the base on insertion of a bone anchor to allow a maximum diameter of a head of a bone anchor to pass and thereafter the split washer retracts overlying the maximum diameter of the head to prevent a bone anchor from backing out.

The split washer is interposed between the base and the dome in the domed chamber, wherein the split washer and the dome when abutted partially overlap combining to prevent a backing out of a bone anchor. The bone anchor locking device can be used with a cervical plate. One or more of the bone locking devices are either formed integral to a cervical plate or made separate and attached and fixed to the cervical plate. For ease of manufacturing, the bone anchor locking device is preferably made separate from the cervical plate. The bone anchor receiving portion has the wall having an external surface for attachment to the cervical plate. The external wall is preferably threaded and configured to be received in a threaded aperture of a cervical plate on assembly to the cervical plate. The inner conical surface of the washer slides against the base or at least partially along the base. The bone anchor locking device may have the bone anchor receiving portion wherein the base includes a release rim or lip projection extending from and adjacent to the aperture opening of the base and the inner surface of the conical split washer slides over the lip or rim. The device can be formed as a subassembly for attachment to any spinal implant device configured to receive the subassembly.

A cervical plate assembly may have two or more apertures for receiving bone anchors for attachment to vertebral bodies. The cervical plate has a plate body or body structure and a locking device. The plate or body structure has two or more openings for receiving a locking device. One locking device is for each opening. The locking device has a bone anchor receiving portion, a dome and a conical split washer positioned interposed between the dome and the bone anchor receiving portion. The split washer and the dome when abutted partially overlap combining to prevent a backing out of a bone anchor. The cervical plate assembly wherein the bone anchor receiving aperture has a bone anchor receiving portion having a through hole sized for receiving and allowing the shank pass and holding the head. The receiving portion has a base extending radially outward and inwardly to a wall. The dome has a center aperture sized to base and a bone anchor, the dome being fixed to the wall and spaced above the base to create a domed chamber. The conical split washer is positioned in the domed chamber having an inner relaxed inner diameter smaller than the head of a bone anchor and an outer diameter larger than the center aperture of the dome and the base. The split washer has an inner conical surface sloped to slide and expand against the base on insertion of a bone anchor to allow a maximum diameter of a head of a bone anchor to pass and thereafter the split washer retracts to prevent a bone anchor from backing out. The bone anchor locking devices are either formed integral to a cervical plate or separated and attached and fixed to a cervical plate. Preferably, the bone anchor locking device is made separate from a cervical plate. The bone anchor receiving portion has the wall having an external surface for attachment to a cervical plate. The external wall is threaded and configured to be received in a threaded aperture or hole of a cervical plate on assembly to the cervical plate. Preferably, the device is formed as a subassembly for attachment to any spinal implant device configured to receive the subassembly. The assembly has a plurality of fixing holes. One fixing hole extends through each of an intersection of the threads of the plate or body structure and the external wall. A plurality of fixing pins are provided. One pin is press fit or otherwise fixed to each of the fixing holes to prevent thread loosening after assembly. The base of the bone anchor receiving portion can include a release rim or lip projection extending from and adjacent to the aperture opening at the base. The release rim or lip projection has an outer wall and upon expansion of the split washer the inner surface of the washer slides along the rim or lip of the base. Also, an inner diameter edge of the washer can be held against the outer wall of the rim or lip to allow removal of a bone anchor.

The invention provides novel methods of use. A method of releasing a bone anchor locking device after the bone anchor has been fully inserted and locked comprises the steps of placing a tubular tool with a chamfered end against an inner diameter surface or edge of a conical split washer; pressing the tool inwardly expanding the washer as an inner conical surface of the washer slides at least partially along the base to a diameter larger than the screw head to unlock the bone anchor; increasing the inside diameter of the tool; and removing the bone anchor by unthreading the bone anchor and passing through the tool. The step of increasing the tool diameter includes removing an inner sleeve leaving a larger diameter outer sleeve.

Another method of releasing a bone anchor locking device after the bone anchor has been fully inserted and locked comprises; placing a tubular tool with a chamfered end against an inner diameter surface or edge of a conical split washer; pressing the tool inwardly expanding the washer as it slides at least partially along the base to a diameter larger than the screw head to unlock the bone anchor; increasing the inside diameter of the tool; expanding the split washer to a diameter larger than a rim or lip diameter of the base; pushing the washer against a wall of the rim or lip; and removing the released bone anchor. The method may have the step removing the tubular tool prior to unthreading the released bone anchor. The base may optionally be conical sloped or tapered.

BRIEF DESCRIPTION OF THE DRAWINGS

The invention will be described by way of example and with reference to the accompanying drawings in which.

DETAILED DESCRIPTION OF THE INVENTION

Figure 1:
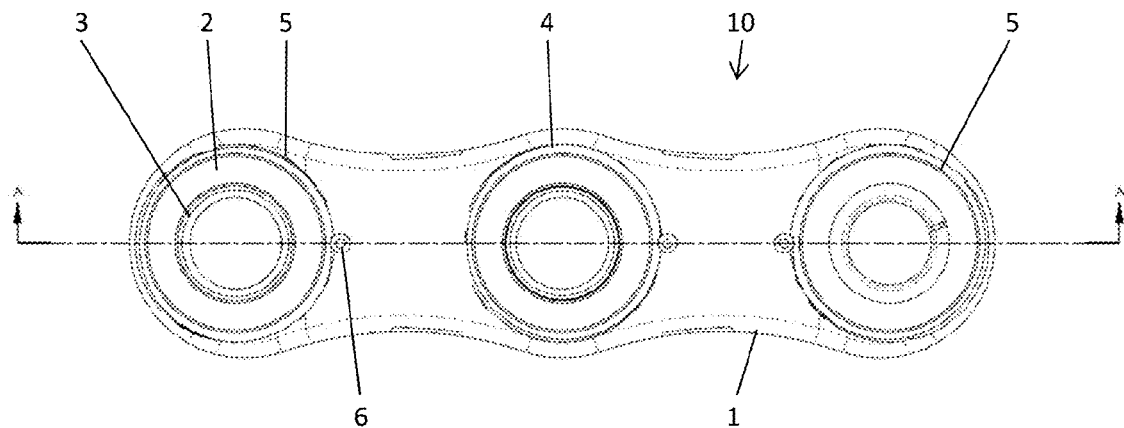
FIG. 1 is a top or plan view of an exemplary cervical plate assembly with a locking device made according to a first embodiment of the present invention.
Figure 2:
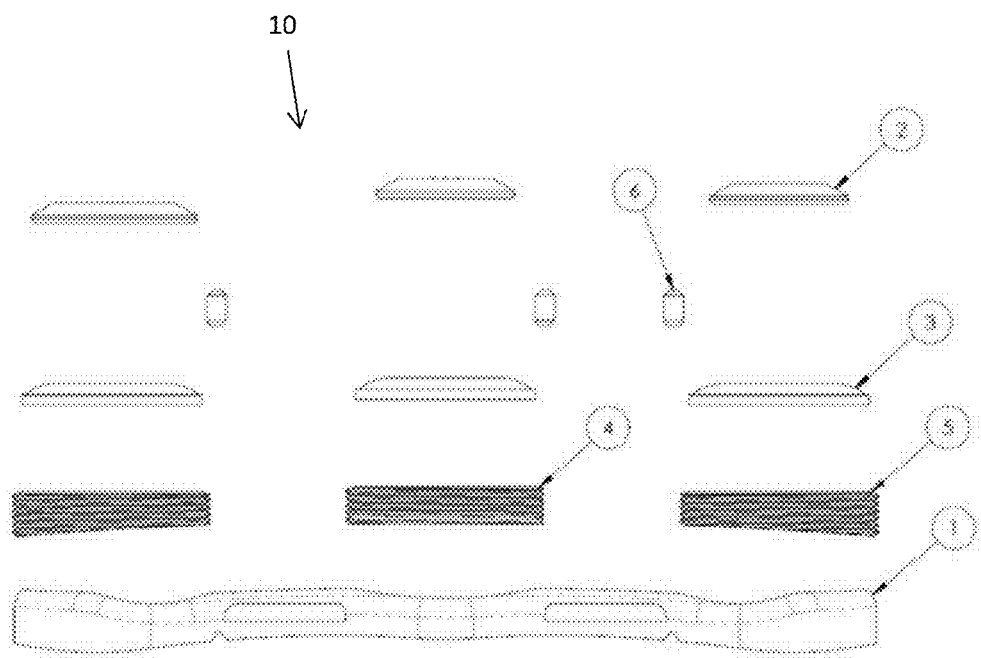
FIG. 2 is an exploded view of the assembly shown in FIG. 1.

With reference to FIGS. 1-5A, a first embodiment of the present invention is illustrated. As shown, a bone anchor locking device 10 for receiving a bone anchor 100 having a shank 110 and an enlarged head 120 is illustrated. The bone anchor locking device 10 as illustrated in FIGS. 1 and 2 is composed of several elements. The first element is a bone anchor receiving portion 4, 5 having a through hole 40 sized for receiving and allowing the shank 110 to pass yet small enough to hold the head 120. The receiving portion 4, 5 has a base 42 extending radially outward and inwardly to a wall 41. This bone anchor receiving portion is designated as reference numbers 4 and 5. As shown, these aperture portions 4, 5 have an external thread 44 which can be threaded to engage a threaded opening 12 in a cervical plate or implant device. The cervical plate or implant device has a body structure 1. It is into the body structure 1 that the bone anchor locking device 10 can be assembled. As shown, the bone anchor locking device 10 further includes a split washer 2 and a dome 3. On assembly, the split washer fits below the dome and above the base 42 of the receiving portion 4, 5. When assembled to the body structure 1, the threaded receiving portions 4, 5 are engaged into the threaded opening 12 of the body structure 1 and pinned using a pin 6 that is pressed into an opening 60 that intersects the threaded portions 12 of the body structure 1 and receiving portions 4, 5 respectively. When so pinned, the assembly 10 cannot twist or unthread itself and is permanently locked to the body structure 1. This pin 6 is press fit into the opening 60 and therefore secures the locking device assembly 10 so that it cannot move or become dislodged.

Figure 3:
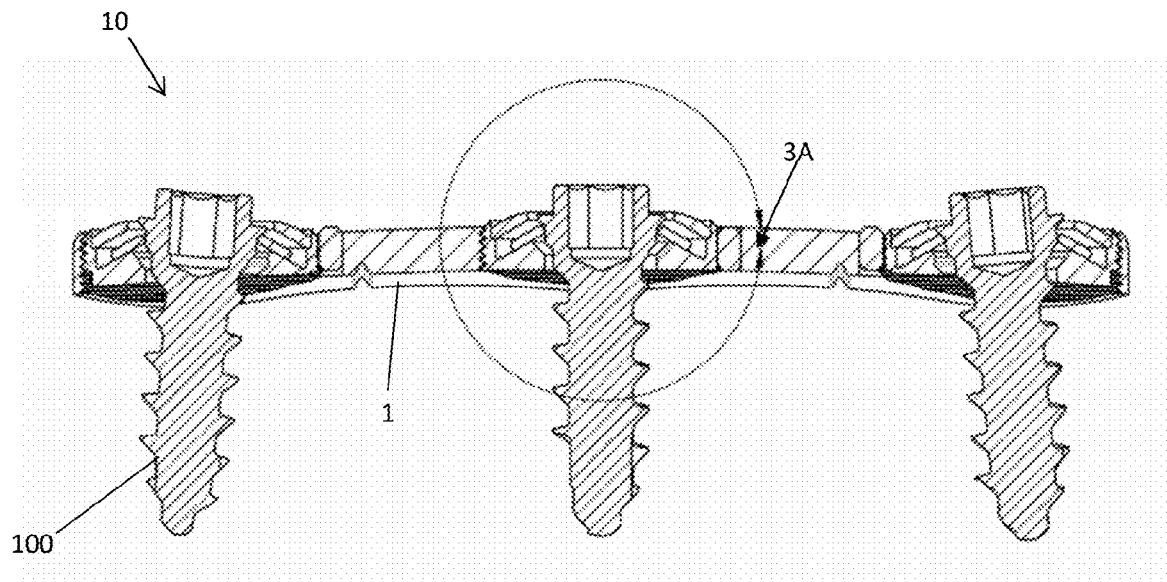
FIG. 3 is a cross sectional view of the first embodiment of the present invention of FIG. 1.
Figure 3A:
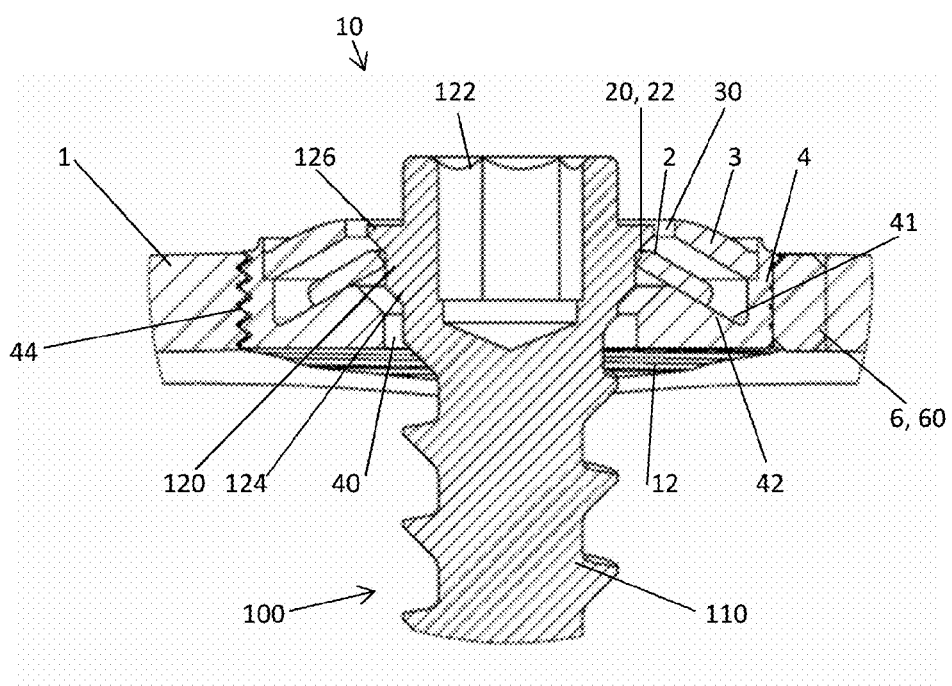
FIG. 3A is an enlarged view of a portion of the embodiment shown in FIG. 3 as shown in location 3A showing a bone anchor at initial assembly.

With reference to FIGS. 3 and 3A, a bone anchor 100 is shown; the bone anchor has a shaft 110 and an enlarged head 120 in FIG. 3A. In these views, the bone anchor 100 is at its initial insertion position, it is extended through the dome 3 opening 30 and is resting against the smaller internal diameter 20 of the conical split washer 2. As shown, an enlarged portion of the head 120 has a maximum diameter at location 126. The spring loaded washer 2 is effectively holding the threaded fastener or bone anchor 100 above the base 42 and the through opening 40 in the receiving portion 4 or 5.

Figure 4:
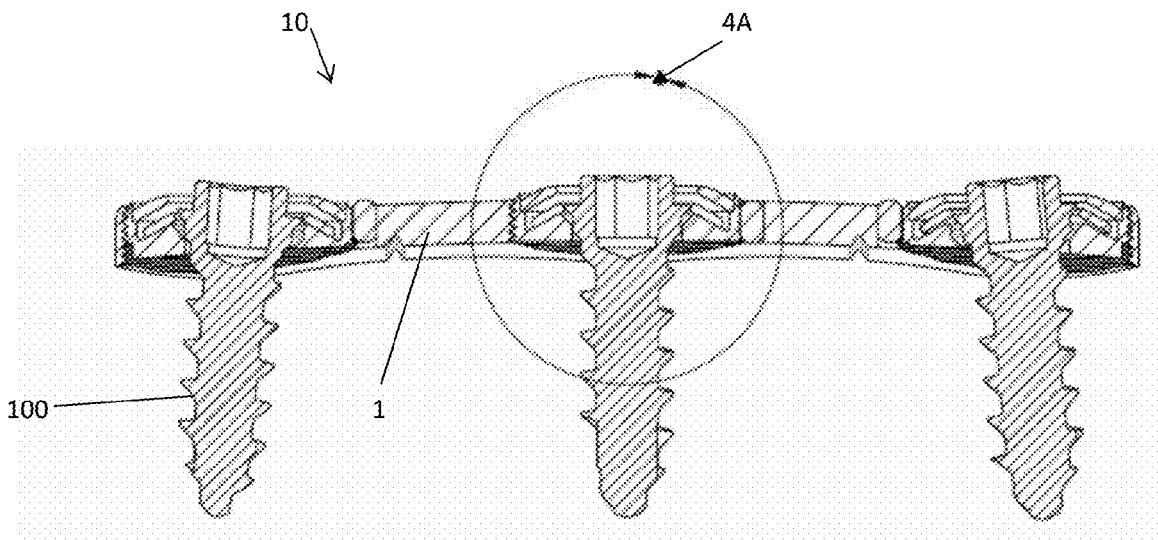
FIG. 4 is a cross section similar to FIG. 3 showing the expansion conical split washer as the maximum diameter of the head of the bone anchor contacts the washer.
Figure 4A:
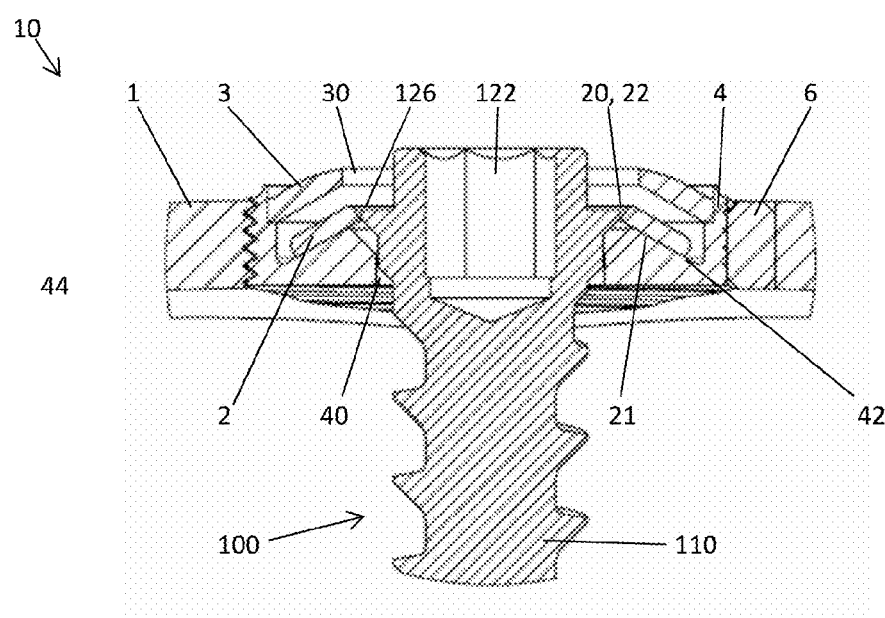
FIG. 4A is an enlarged view taken in the location 4A of FIG. 4.

With reference to FIGS. 4 and 4A, the bone anchor 100 is shown being threadingly engaged into a vertebrae (not illustrated). In this position, the spring washer 2 is being pushed inwardly and expanded along the base 42 towards the maximum diameter portion 126. As this occurs, the washer 2 inside diameter 20 enlarges along an inner edge 22. As further shown, as this diameter 20 increases, the inner conical surface 21 of the split washer 2 is sliding along the base 42 of the receiving portion 4. As shown the split washer 2 is shown resting and abutting against the surface 42 as it slides and expands to open as the threaded fastener moves inwardly during the engagement of the bone. This holds true regardless of the angles of the base 42 and the inner conical surface 21 of the conical split washer 2 are the same. If these angles are different, but directionally similarly sloped then at least a portion of the inner surface of the washer 2 will slide along the base 42. As shown, the base 42 has a conical sloped surface. The base 42 of the illustrated first embodiment, while showing this feature can be configured in any number of shapes as long as they provide a means for the inner conical surface to slide against.

Figure 5:
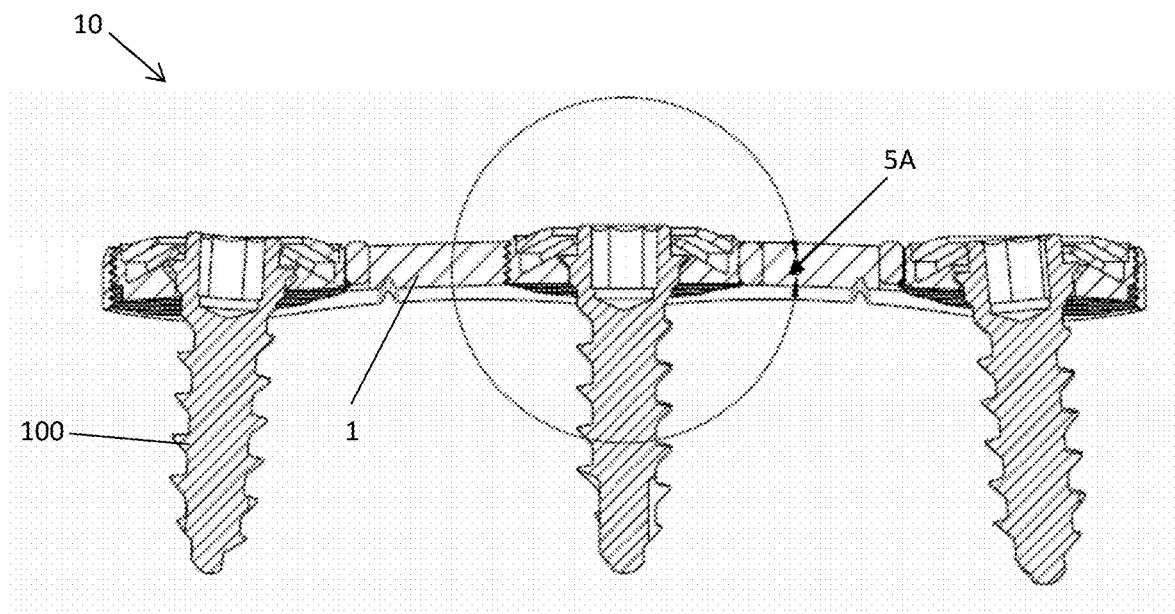
FIG. 5 is a cross sectional view of the fully inserted bone anchors showing the heads moved past the conical split washers and the washers retracted back to size overlying the maximum diameters of the heads.
Figure 5A:
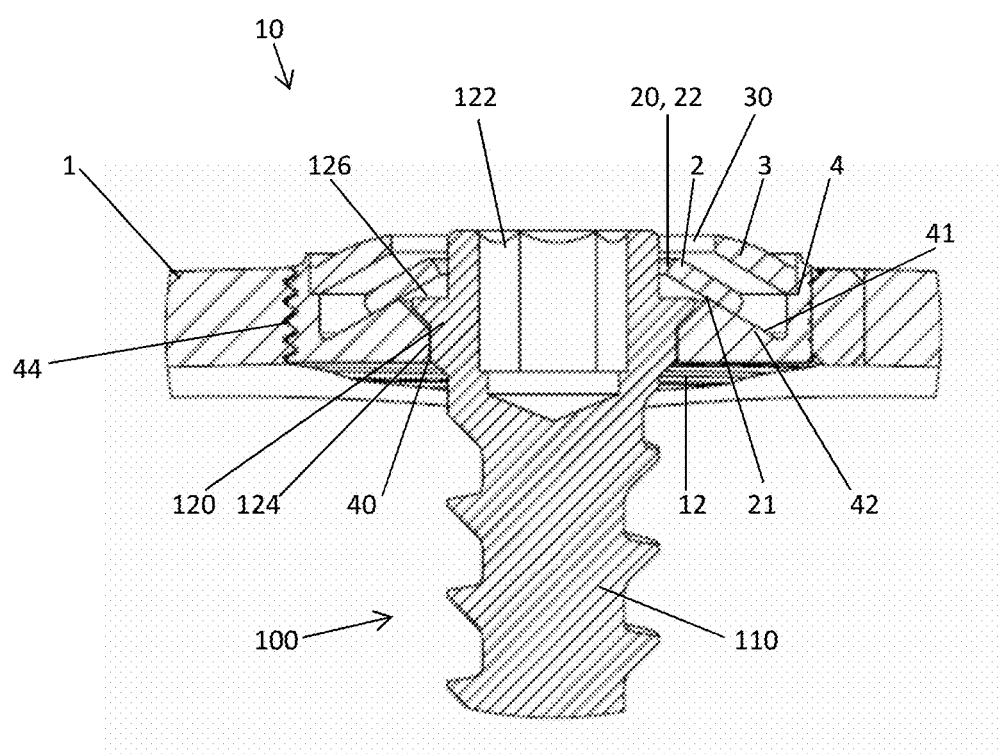
FIG. 5A is an enlarged view taken from FIG. 5 at location 5A.
Figure 6:
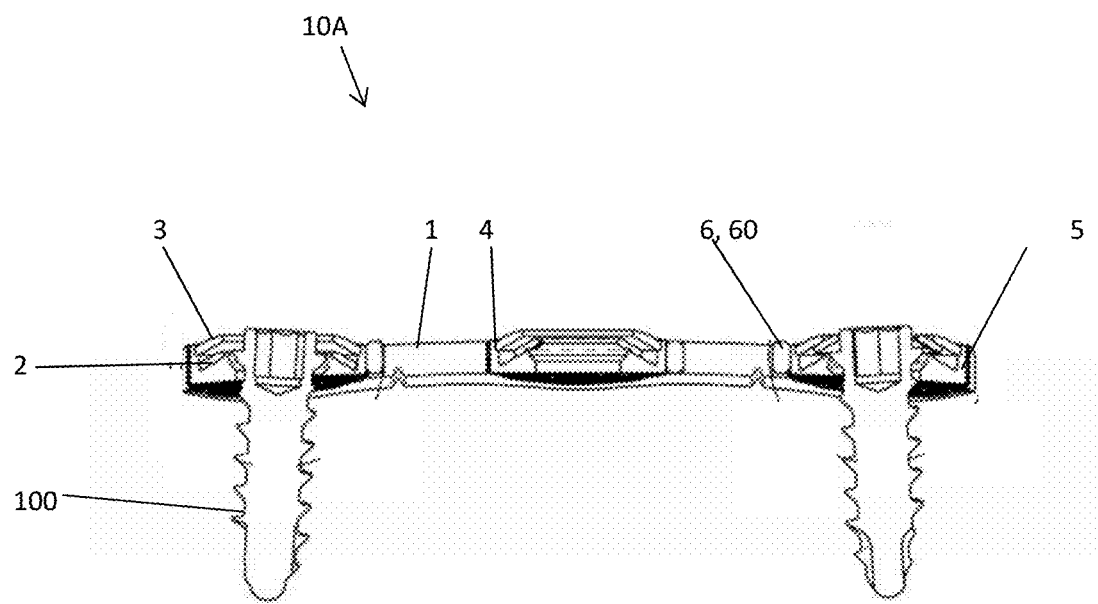
FIG. 6 is a second embodiment of the present invention shown in cross section.

With reference to FIGS. 5 and 5A, the bone anchor 100 is shown fully inserted. At this point, the large or maximum diameter portion of the head 120 at location 126 is allowed to be passed over past the conical split washer 2. When this occurs, the expanded diameter 20 of the conical split washer 2 is released and returned to the original opening size 20 of the split washer 2. As shown, the split washer 2 is now partially overlying locking the head portion 120 of the shank 110 and preventing it from backing out. Assuming that the conical split washer 2 is directionally pushed by the head 120 of the screw or bone anchor 100, it is noted that the dome 3 that is securely fastened to the inner wall 41 of the receiving portion 4, 5 further reinforces the washer 2 helping to resist any back-out of the threaded fastener or anchor 100.

Referring back to FIG. 3A, as illustrated, the receiving portion 4, 5 has threads 44 that engage threads 12 through the opening in which the receiving portion 4, 5 is received. As further shown, the pin 6 has been inserted into the plate 1 as previously discussed thereby locking the receiving portion 4, 5 in its position as illustrated. As shown the receiving portion 4, 5 will have a central aperture opening 40 extending therethrough. This aperture 40 is designed to allow the shank 110 of the bone anchor 100 to pass. As illustrated this opening 40 is contoured in such a fashion that as the bone anchor 100 is fully inserted, the head 120 of the fastener will abut and be seated against the base 42. As shown, the base 42 has been modified in this example to match and be complimentary to the shape of the head 120. This base 42 provides a seat upon which the head 120 rests upon full insertion. The head 120 as further illustrated in the figures, has a central opening 122; this central opening 122 receives a driving mechanism or drive that can be inserted to rotate and twist the screw or bone anchor 100 into the bone. As mentioned, the interior portion of the head 120 has a shape 124 that is complimentary to the base 42.

An important feature of this first embodiment 10 and its exemplary plate 1 is that the conical split washer 2 can be slid partially or entirely along the base surface 42 in such a fashion that the washer 2 expands as a direct result of the radially increasing and directionally inward along the base 42 forcing the washer 2 to open and enlarge the diameter 20 so the maximum diameter 126 of the head 120 can pass and be locked into the washer 2 as the washer 2 returns to its original shape sliding back up the base 42 once past the location 126. A secondary feature of great benefit is that the dome 3 which has been fixed to the inner wall 41 of the receiving portion 4, 5 means that the resistance to pull out of the threaded bone anchor 100 is supported not only by the washer 2, but by the washer 2 underlying the overlapping dome 3. The dome 3 itself will provide additional resistance to any back-out.

Figure 7:
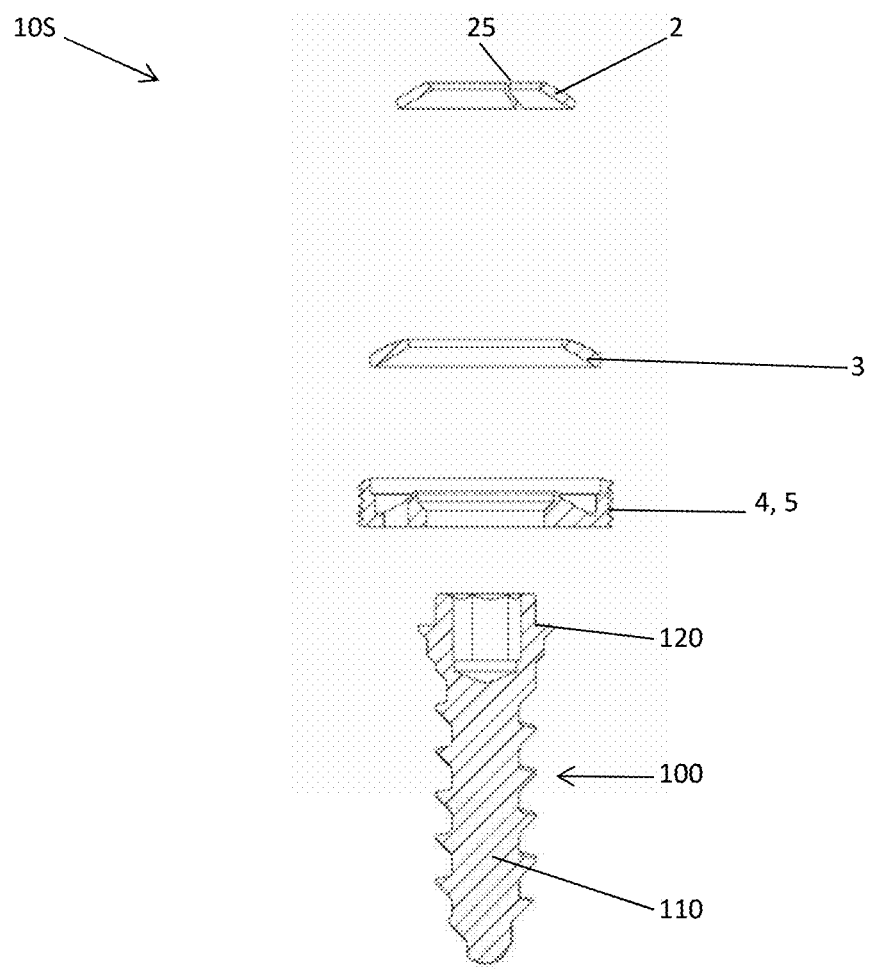
FIG. 7 is an exploded cross sectional view of the locking device made in accordance with the second embodiment of FIG. 6.

With reference to FIGS. 6-10A, a second embodiment of the present invention is illustrated. This embodiment features the bone anchor locking device 10A shown attached to an exemplary cervical plate 1 with all the elements previously discussed including the dome 3, conical split washer 2, receiving portion 4, 5, and the fixing pins 6 to secure bone anchors 100. As shown in FIG. 7, this subassembly can be referred to as 10S, this subassembly 10S is a combination of the receiving portion 4, 5, the dome 3 and the conical split washer 2 wherein the split 25 is illustrated. On assembly, this creates an entire bone anchor locking device subassembly 10S. Additionally, but not part of the bone anchor locking device subassembly 10S is shown the bone anchor 100. This exemplary bone anchor can be substituted with any number of bone anchors with any number or style of threads on the shank 110 and any style of head 120. The head 120 as shown is similar to that shown in FIGS. 1-5A, as previously discussed; however it is understood that this head shape 120 can be a spherical dome, a polyaxial head or any number of shapes having a maximum diameter. The important aspect is the subassembly 10S can be provided to fit with any implant device or any cervical plate or implant used in spinal vertebrae attachment where bone anchors are required. While the bone anchor 100 does not make part of the subassembly 10S, it is important to note that the locking device subassembly 10S whether it has the features of the first embodiment or the second embodiment it is provided such that it can be attached to any implant device adapted with the threads 12 to engage the external threads 44 shown on the receiving portions 4 and 5.

Figure 8:
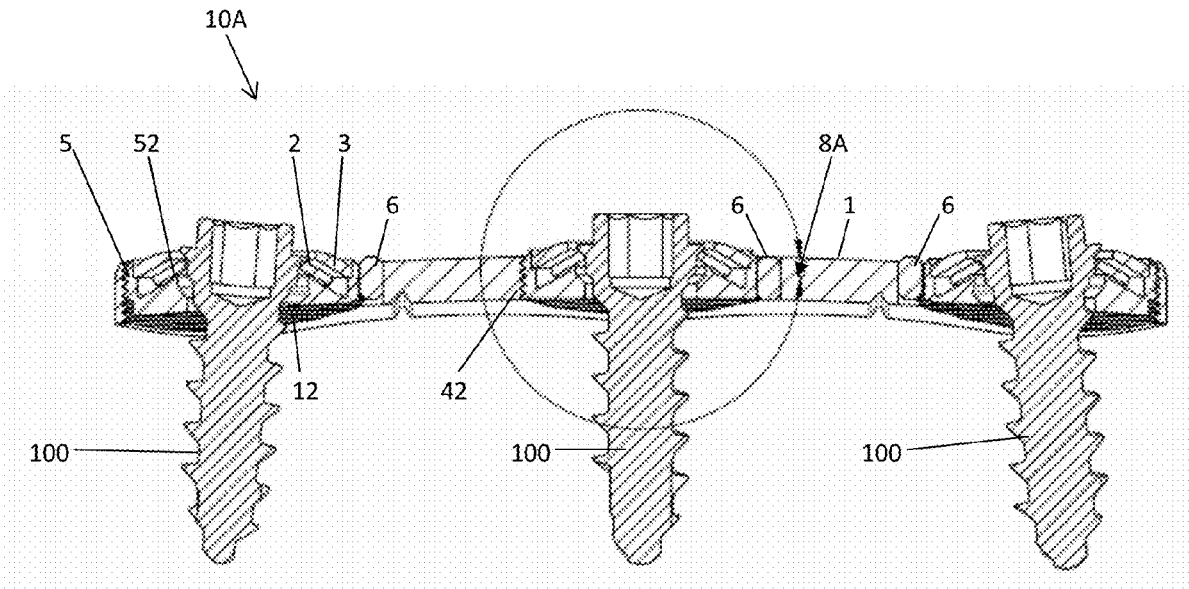
FIG. 8 is a cross sectional view of the second embodiment of the present invention of FIG. 1.
Figure 8A:
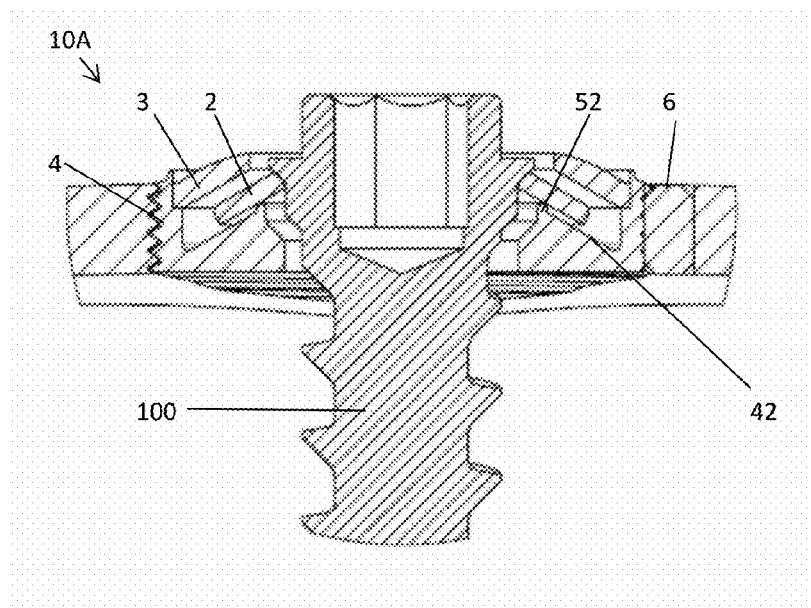
FIG. 8A is an enlarged view of a portion of the embodiment shown in FIG. 8 as shown in location 8A showing a bone anchor at initial assembly.
Figure 9:
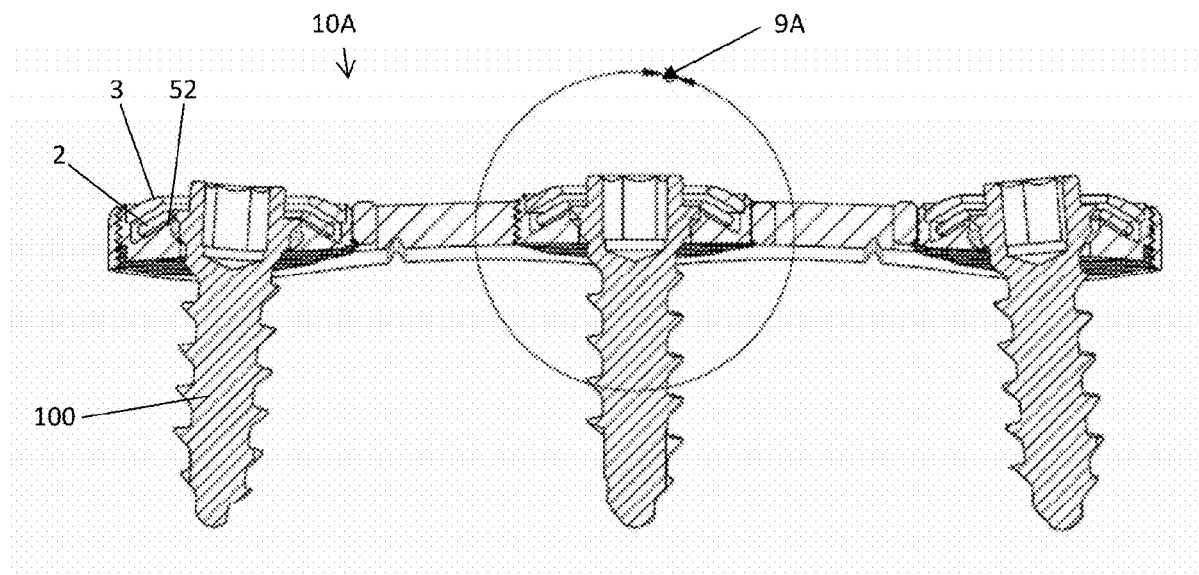
FIG. 9 is a cross section similar to FIG. 8 showing the expansion conical split washer as the maximum diameter of the head of the bone anchor contacts the washer.
Figure 9A:
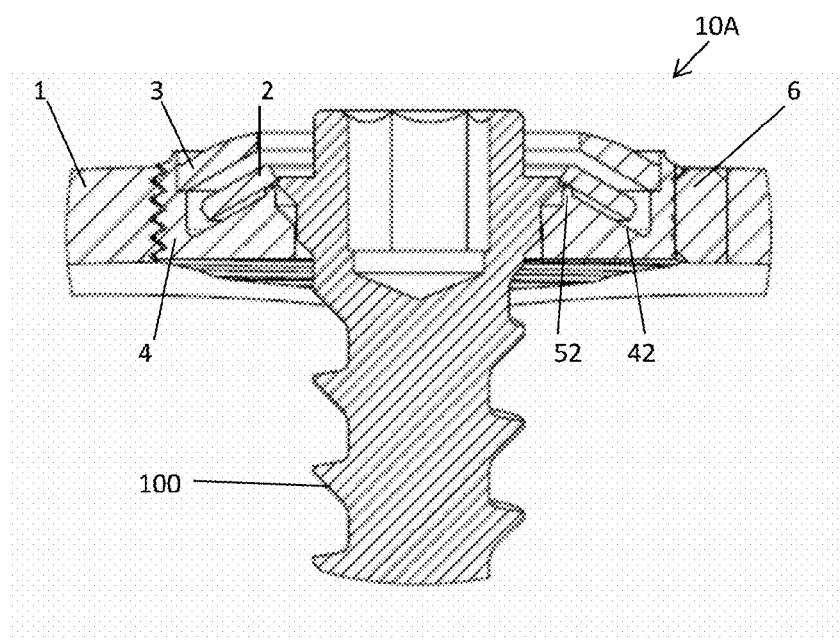
FIG. 9A is an enlarged view taken in the location 9A of FIG. 9.
Figure 10:
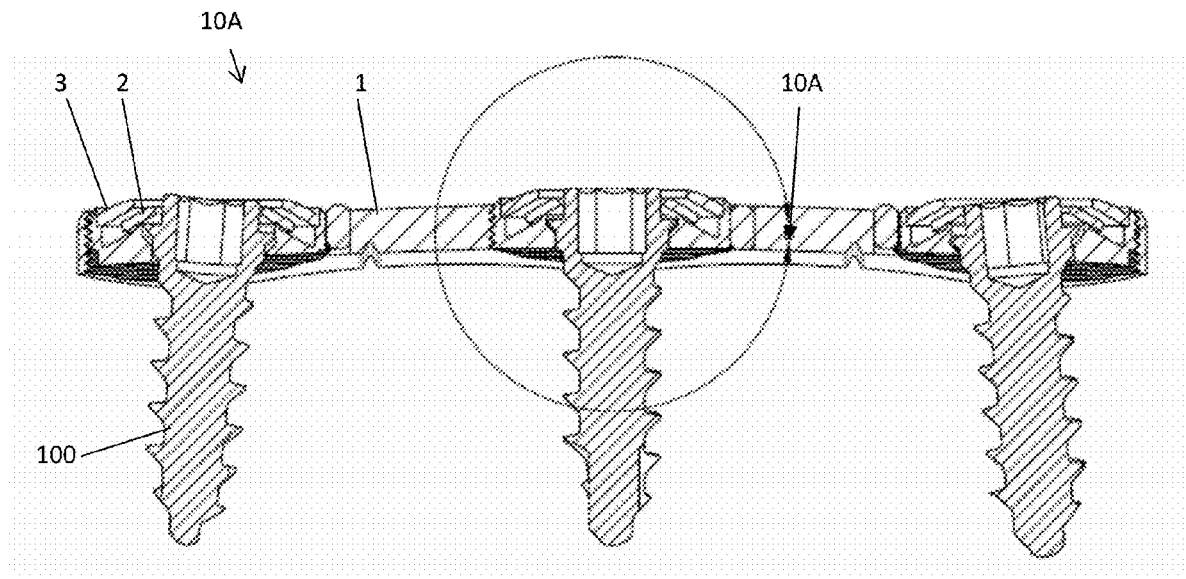
FIG. 10 is a cross sectional view of the fully inserted bone anchors showing the heads moved past the conical split washers and the washers retracted back to size overlying the maximum diameters of the heads.
Figure 10A:
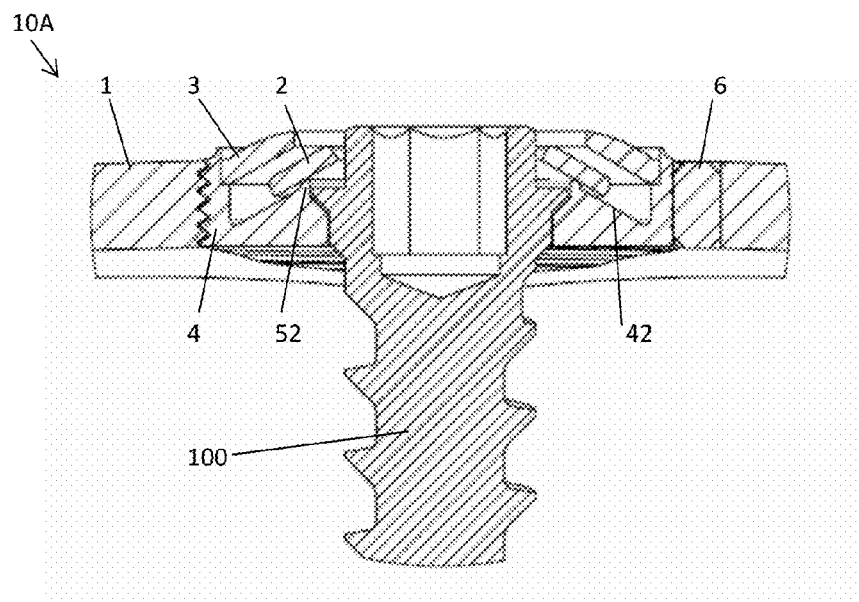
FIG. 10A is an enlarged view taken from FIG. 10 at location 10A.

With reference to FIGS. 8, 8A, 9, 9A, 10, 10A, the second embodiment is shown wherein the anchor 100 in FIGS. 8 and 8A is in the initial position. In this case however, as illustrated the base 42 of the receiving portion 4, 5 includes a rim or lip 52 projecting upwardly from the sloped surface 42. In this fashion, the split washer 2 is shown resting on this rim or lip 52. As shown the rim or lip 52 is supporting the split washer 2 during the initial entry of a bone anchor 100. As the bone anchor 100 is engaged into the vertebrae (not shown) inner conical surface 21 of the split washer 2 rides against this rim or lip 52 as it is pushed and extends downwardly in a direction similar to or the same as the base 42. The rim or lip 52 may hold the washer 2 slightly gapped above the surface of the base 42 on at least part of the surface closest to the rim or lip 52. It is understood that the washer 2 depending on the shape of the screw head being inserted can at least partially contact and slide down the surface of the base 42 or the rim or lip 52 of the base 42. In any event, it will directionally move in a similar direction to the slope of the conical inner surface 21 of the washer 2 as the head 120 of screw 100 pushes the split washer 2 into an expanded condition as illustrated in FIGS. 9 and 9A. As best illustrated in 9A when the maximum diameter is achieved, the split washer 2 is still sitting above on the rim or lip 52 slightly gapped from the rest of the base portion 42. Upon further and complete insertion of the bone anchor 100, the washer 2 will then slide back into position similar to the first embodiment wherein the washer 2 returns to its normal size diameter 20 and the inner edge 22 of the split washer 2 will hold the maximum diameter of the head 120 in its retained and locked position preventing back-out. As previously noted in this embodiment, the dome 3 will assist in resisting any back-out of the anchor 100.

Figure 11:
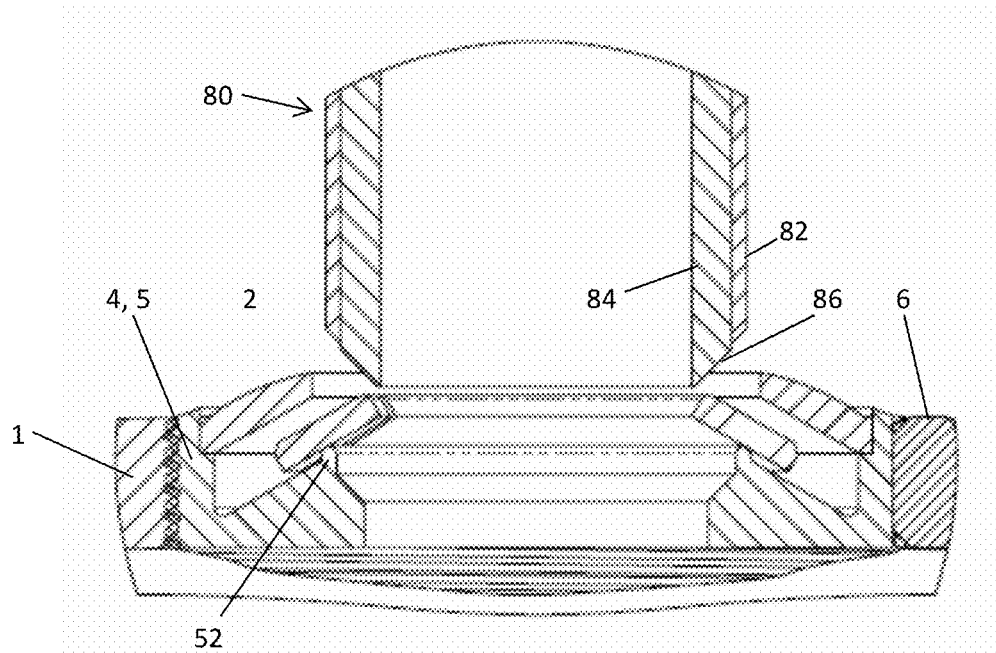
FIG. 11 is a cross sectional view of a locking device release tool for expanding the conical split washer.
Figure 12:
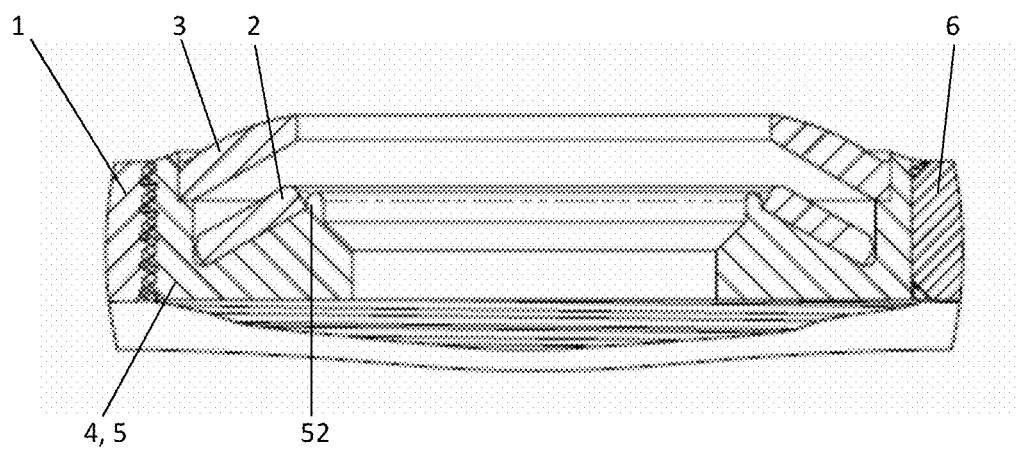
FIG. 12 is an enlarged cross section showing the feature of the second embodiment wherein the conical washer can be held expanded by the release ring.

With reference to FIGS. 11 and 12, this rim or lip portion 52 of the base 42 as illustrated is shown with a locking release tool 80. For better visualization, the bone anchor screw 100 and its head have been removed from the assembly so that the observation can be made as to how the tool 80 can expand the split washer 2 in such a fashion that it will open directionally the same as is accomplished with the head of the threaded fastener. However, as the tool 80 pushes down, it has a chamfered surface 86, this chamfered surface 86 extends along the entire tool 80. As shown, the tool 80 in this embodiment has an inner sleeve 84 and an outer sleeve 82. This allows the tool 80 to have a small diameter on the inner sleeve 84 as it initially contacts the locking washer 2 and slides down against the inner edge 22 of the inner diameter 20 of the conical split washer 2 and pushes it directionally parallel to the conical slope. As the tool 80 is pushed further it is shown in FIG. 12 how the inner edge 22 of the washer 2 will abut at the diameter 20 against the rim 52 wall. When the inner edge 22 of the washer 2 butts against this surface or wall, the washer 2 is docked on the base 42 retained in a fully open position by the rim or lip 52. It is in this position where a surgeon can take a retraction tool or driver and unthread the bone anchor 100 from the vertebrae. In this fashion, the locking device 10 provides a releasable feature. As illustrated, the tool 80, will also work with the first embodiment. However, with the first embodiment, the tool 80 must remain in place and the inner sleeve 84 removed when the maximum diameter of the tool 80 is achieved. The maximum inside diameter of the outer sleeve 82 is larger than the maximum diameter 126 of the head of the screw 100. So when this inner sleeve 84 is removed the outer sleeve 82 can hold the conical split washer 2 in place and a driver can be used to unthread the bone anchor 100 releasing it from the vertebrae while holding the tool 80 in place. The second embodiment eliminates the need to hold the tool 80 in place as the conical split washer 2 can be docked and positioned abutting the lip 52 of the base 42 of the receiving portion 4, 5 to keep it in a fully open position in the absence of any tool being positioned as the surgeon removes the fastener 100. In either case, the tool 80 will work with either embodiment increasing the diameter such that the split washer 2 will not interfere with the release of a threaded fastener 100 once attached to the bone. This is important should a surgeon need to remove any of the fasteners previously installed such that the cervical plate or the implant device that is being anchored, can be released from the locking device.

By expanding the conical washer 2 by pressing the washer conical inner surface 21 against the base 42 greatly reduces the forces required to enlarge the diameter of the conical split washer 2. The forces are tangential to the slope of the surface 21. This means that fraction of the forces acting on the threads of the bone anchor as they engage the bone are less making it easier to drive the bone anchor without stripping the bone threads as compared to prior art locking devices.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A bone anchor locking device for receiving a bone anchor having a shank and an enlarged head, the device comprises:
    a bone anchor receiving portion having a through hole sized for receiving and allowing the shank to pass and holding the head, the receiving portion having a base extending radially outward and inwardly to a wall;
    a dome having a center aperture sized to pass the bone anchor, the dome being fixed to the wall and spaced above the base to create a domed chamber; and
    a conical split washer positioned in the domed chamber having an inner relaxed inner diameter smaller than the head of the bone anchor and an outer diameter larger than the center aperture of the dome and the through hole opening at the base, the split washer having an inner conical surface sloped to slide and expand against at least a portion of the base on insertion of the bone anchor to allow a maximum diameter of the head of the bone anchor to pass and thereafter the split washer retracts to prevent the bone anchor from backing out.

2. The bone anchor locking device of claim 1 wherein the split washer is interposed between the base and the dome in the domed chamber.

3. The bone anchor locking device of claim 2 wherein the split washer and the dome, when abutted, partially overlap combining to prevent a backing out of the bone anchor.

4. The bone anchor locking device of claim 3 wherein one or more of the bone anchor locking devices are either formed integral to a cervical plate or made separate and attached and fixed to the cervical plate.

5. The bone anchor locking device of claim 4 wherein the bone anchor locking device is made separate from the cervical plate.

6. The bone anchor locking device of claim 5 wherein the bone anchor receiving portion has the wall having an external surface for attachment to the cervical plate.

7. The bone anchor locking device of claim 6 wherein the external surface is threaded and configured to be received in a threaded aperture of the cervical plate on assembly to the cervical plate.

8. The bone anchor locking device of claim 1 wherein the inner conical surface of the washer slides against the base.

9. The bone anchor locking device of claim 1 wherein the base of the bone anchor receiving portion includes a release rim or lip projection extending from and adjacent to the through hole opening at the base.

10. The bone anchor locking device of claim 1 wherein the device is formed as a subassembly for attachment to any spinal implant device configured to receive the subassembly.

11. A cervical plate assembly having two or more apertures for receiving bone anchors for attachment to vertebral bodies, the cervical plate assembly comprises:
    a cervical plate or body structure having two or more openings for receiving a locking device;
    a locking device for each of the two or more openings, the locking device having a bone anchor receiving portion, wherein the bone anchor receiving portion has a bone anchor receiving aperture having a through hole sized for receiving and allowing a shank to pass and holding a head, the receiving portion having a base extending radially outward and inwardly to a wall, a dome, wherein the dome has a center aperture sized to pass the bone anchor, the dome being fixed to the wall and spaced above the base to create a domed chamber and a conical split washer positioned interposed between the dome and the bone anchor receiving portion, wherein the conical split washer is positioned in the domed chamber having an inner relaxed inner diameter smaller than the head of the bone anchor and an outer diameter larger than the center aperture of the dome and the through hole opening at the base, the split washer having an inner conical surface sloped to slide and expand against the base on insertion of the bone anchor to allow a maximum diameter of the head of the bone anchor to pass and thereafter the split washer retracts to prevent the bone anchor from backing out; and
    wherein the split washer and the dome, when abutted, partially overlap combining to prevent a backing out of a bone anchor.

12. The cervical plate assembly of claim 11 wherein the locking devices are either formed integral to the cervical plate or separated and attached and fixed to the cervical plate.

13. The cervical plate assembly of claim 11 wherein the bone anchor locking device is made separate from the cervical plate.

14. The cervical plate assembly of claim 13 wherein the bone anchor receiving portion has the wall having an external surface for attachment to the cervical plate.

15. The cervical plate assembly of claim 14 wherein the external surface is threaded and configured to be received in a threaded aperture or hole of the cervical plate on assembly to the cervical plate.

16. The cervical plate assembly of claim 15 wherein the assembly has a plurality of fixing holes, one hole extending through each of an intersection of the threads of the plate or body structure and the external surface; and a plurality of fixing pins, one pin being press fit or otherwise fixed to each of the fixing holes to prevent thread loosening after assembly.

17. The cervical plate assembly of claim 11 wherein the device is formed as a subassembly for attachment to any spinal implant device configured to receive the subassembly.

18. The cervical plate assembly of claim 11 wherein the base of the bone anchor receiving portion includes a release rim or lip projection extending from and adjacent to the through hole opening at the base.

19. The cervical plate assembly of claim 18 wherein the release rim or lip projection has an outer wall and upon expansion of the split washer an inner diameter surface of the split washer can be held against the outer wall of the rim or lip to allow removal of the bone anchor.

\* \* \* \* \*